United States Patent [19]

Collins

[11] Patent Number: 5,013,555

[45] Date of Patent: May 7, 1991

[54] AGENT FOR DESENSITIZING MAN AND/OR ANIMALS AGAINST AN ALLERGEN

[76] Inventor: Amy L. T. Collins, 7605 Ridgecrest Dr., Alexandria, Va. 22308

[21] Appl. No.: 320,795

[22] Filed: Mar. 9, 1989

Related U.S. Application Data

[63] Continuation-in-part of Ser. No. 190,378, May 5, 1988, abandoned.

[51] Int. Cl.$^5$ .................... A61K 37/22; A61K 35/78; A61K 35/58
[52] U.S. Cl. ............................... 424/450; 424/195.1; 424/539; 424/542; 424/688; 514/885
[58] Field of Search ................... 424/450, 95, 195.1, 424/157, 539, 542, 688; 5.4/885

[56] References Cited

U.S. PATENT DOCUMENTS

| | | | |
|---|---|---|---|
| 4,387,091 | 6/1983 | Vijay et al. | 424/88 |
| 4,395,394 | 7/1983 | Wolf et al. | 424/88 |

OTHER PUBLICATIONS

Alving, C. R. et al, "Preparation and Use of Liposomes in Immunological Studies", in Liposome Technology, vol. II (1984), pp. 157–175.
Alving, C. R. et al., "Effectiveness of Liposomes as Potential Carriers of Vaccines: Applications to Cholera Toxin and Human Malaria Sporozoite Antigen", Vaccine, 4:166–172 (1986).
August, J. R., "The Reaction of Canine Skin to the Intradermal Injection of Allergenic Extracts," J. Am. An. Hosp. Assn., 18:157–163.
Ballou, W. R. et al., "Safety and Efficacy of a Recombinant DNA Plasmodium Falciparum Sporozoite Vaccine," The Lancet, i:1277–1281 (1987).
Edelman, R., "Vaccine Adjuvants," Rev. Infect. Dis., 2:370–383 (1980).
Gregoriadis, G. et al., "Entrapment of Proteins in Liposomes Prevents Allergic Reactions in Pre-Immunised Mice," FEBS Letters, 45:71–74 (1974).
Nesbitt, G. H. et al., "Aeroallergens," Compend. Cont. Educ. Prac. Vet., 6:63–68 (1984).
Nesbitt, G. H. et al., "Canine Atopy. Part I, Etiology and Diagnosis," Compend. Cont. Educ. Pract. Vet., 6:73–84 (1984).
Alving, C. R., "Liposomes as Carriers for Vaccines" in Liposomes, Ostro, M. J. (ed. 1987), pp. 195–218.
Richards, R. L. et al, "Liposomes as Carriers for a Malaria Peptide Vaccine: Development Aspects", in Immunopharmacology of Infectious Diseases: Vaccine Adjuvants and Modulators of Non-Specific Resistance, pp. 171–180 (1987).
Richards, R. L. et al., "Liposomes, Lipida, and Aluminum Hydroxide Enhance the Immune Response to a Synthetic Malaria Sporozoite Antigen," Infect. Immun., 56:682–686 (1988).
Lopez-Berestein, G. et al., "Liposomac Amphotericin B for the Treatment of Systemic Tunsac Infections in Patients".
Coune, A. et al., "IV Administration of a Water-Insoluble Antimitotic Compound Entrapped in Liposomes, Preliminary Report on Infusion of Large Volumes of Liposomes to Man," Cancer Tr. Rept., 67:1031–1033 (1983).
"With Cancer: A Preliminary Study," J. Infect. Dis., 151:704–710 (1985).

Primary Examiner—John W. Rollins

[57] ABSTRACT

An agent for desensitization of man and/or animals against an allergen comprising liposomes that comprise the allergen is provided together with a method for inducing desensitization by administration of the agent.

19 Claims, No Drawings

AGENT FOR DESENSITIZING MAN AND/OR ANIMALS AGAINST AN ALLERGEN

This application is a continuation-in-part of application Ser. No. 190,378, filed May 5, 1988, now abandoned.

BACKGROUND OF THE INVENTION

This invention relates to an agent for desensitizing man and/or animals against an allergen comprising liposomes that comprise an allergen. This invention also relates to a method for desensitization by administration of such an agent into man and/or animals.

Allergy is an ailment that affects millions of individuals worldwide. Attempts to desensitize an individual against a material that causes an allergic response (hereafter designated as an "allergen") by injection of measured dosages of the allergen heretofore has failed to achieve complete relief of allergy symptoms reproducibly in all allergic individuals. An allergic response is a term of art and has a well-defined meaning. Within the context of the present invention, an allergic response includes, in particular, at least one of the features of (1) production of an abnormally high level of IgE in an individual's serum, (2) immunologic interaction between an allergen, an individual's IgE and leukocytes, resulting in release of histamines, (3) production of hives, rashes, wheel and flare and similar dermatological manifestation of hypersensitivity and (4) anaphylaxis.

Until the present invention, an individual who wishes to become desensitized against an allergen has to submit himself/herself to injections of measured doses of the allergen, first administered at weekly or biweekly intervals, then gradually decreases to bimonthly or monthly intervals throughout the year. Such injections generally commence with a small dose of the allergen and then gradually increasing the dosage until a maximally-tolerated maintenance dose is achieved. The individual is then kept on a maintenance dose of the allergen indefinitely or until the individual no longer exhibits an allergic reaction to the allergen.

Liposomes have been used recently as carriers of vaccines, e.g., a vaccine against a malarial parasite as described by Alving et al., in *Vaccine*, 4:166–172 (1986) and a vaccine against Epstein-Barr ("EB") virus as described by Alving in "Liposomes as Carriers for Vaccines" in *LIPOSOMES FROM BIOPHYSICS TO THERAPEUTICS*, M. J. Ostro ed. (Marcel Dekker, Inc. N.Y. 1987).

Liposomes have also been used as carriers of drugs, e.g., amphotericin B as described by Lopez-Berestein et al., in *J. Infect. Dis.* 151:704–710 (1985) and an antimitotic agent as described by Coune et al., in *Cancer Treat. Rep.* 67:1031–1033 (1983).

Until the present invention, there has been no report of using liposome comprising an allergen to desensitize an individual against the allergen.

SUMMARY OF THE INVENTION

It is an object of the present invention to provide an agent for desensitization of man and/or animals against an allergen that is more effective than the existing agents.

It is also an object of the present invention to provide an agent for desensitization of man and/or animals that can be administered with less frequency than the existing agents.

It is a further object of the present invention to provide a method for desensitization of man and/or animals by use of an agent, as described above, that can be applied for a wide variety of allergens.

It is still another object of the present invention to provide a method for desensitization, as described above, that can be applied with relative ease.

In accomplishing these and other objects, there has been provided an agent for desensitization of man and/or animals against an allergen comprising liposomes that comprise an allergen.

In accordance with another aspect of the present invention, there has been provided an agent as above, wherein said liposomes comprise an adjuvant.

In accordance with a further aspect of the present invention, there has been provided an agent as above, wherein said allergen is at least one selected from the group consisting of food allergens, drug allergens, venom allergens, plant allergens, fungal allergens, bacterial allergens and animal allergens.

In accordance with yet another aspect of the present invention, there has been provided a method for desensitization of man and/or animals by administration of an agent as described above.

In accordance with still another aspect of the present invention, there has been provided a method as above, wherein said agent is administered orally and/or injected either intramuscularly, intradermally, intravenously, intraperitoneally or subcutaneously.

In accordance with as yet another aspect of the present invention, there has been provided a method as described above, wherein said agent is administered at intervals of at least about 4 weeks.

Further objects, features and advantages of the present invention will become apparent from the following detailed description. It should be understood, however, that the detailed description, while indicating preferred embodiments of the invention, is given by way of illustration only, since various changes and modifications within the spirit and scope of the invention will become apparent to those skilled in the art from this detailed description.

DETAILED DESCRIPTION OF THE PREFERRED EMBODIMENTS

It has been discovered that liposomes that comprise allergen can be effective in desensitization of man and/or animals against an allergen. In the context of the present invention, desensitization means the process by which an individual, man or animal, is rendered incapable of exhibiting any physical symptom of an allergic response such as sneezing, itchy eyes and throat, nasal congestion, etc., or the process by which such physical symptoms or the specific IgE response to the allergen, in man or animal, is reduced.

Suitable allergens for use in the context of the present invention includes food allergens, drug allergens, venom allergens, plant allergens, fungal allergens, bacterial allergens, animal allergens, other allergens from naturally-occurring or synthetic substances and extracts thereof, either in an unconjugated form or in the form of a hapten conjugated to a carrier.

Food allergens include, for example, seafood, strawberries, fresh fruit and vegetables. Drug allergens include, for example, penicillin and insulin. Venom allergens include, for example, bee and wasp venoms. Plant allergens include, for example, tree pollen, grass pollen and weed pollen. Fungal allergens include, for example, mold spores. Animal allergens include, for example, dander or saliva from dogs, cats, horses, etc.

Allergens within the present invention can be used in the form currently being used by physicians, i.e., in the form used for "allergy shots" by allergists, for desensitization purposes, or can be an antigenic portion of such, in the form of a hapten, conjugated to a carrier molecule. A suitable carrier molecule is preferably one that will increase the immunogenicity of the hapten without eliciting an immune response to the carrier. Bovine serum albumin ("BSA"), thyroglobulin and tetanus toxoid can be used as carriers in the present invention. The hapten molecule can be conjugated to the carrier in accordance to standard laboratory procedures.

The dose of allergen to be used in the present invention can be determined by routine experimentation on an individual basis using establish immunological techniques. For example, determination can be done by skin test, using the liposomes that comprise an allergen, prepared as described below, as the testing agent. The maximum dose of liposome-encapsulated allergen that does not elicit a positive reaction by accepted standards, for example, a wheel and flare reaction greater than, e.g., 5 mm in diameter, can be used as the immunizing dose. The progress of desensitization can be monitored by periodic determination of serum immunoglobulin levels and leukocyte response to allergen in vitro. In the absence of a positive reaction to the immunizing dose of liposomes comprising the allergen, for example, within 15-20 minutes of injection, the immunizing dose can be progressively increased, e.g., by ten-fold, with the next immunizing dose.

In the alternative, the initial dose of allergen to be used in the present invention can be a conventional low dose, e.g., ragweed pollen in an amount comprising 0.1 microgram of antigen E can be used as in Creticos et al., *J. Allergy Clin. Immunol.* 73:94-104 (1984), the contents of which are incorporated herein by reference. Similarly, 0.01 microgram of bee, hornet or wasp venom can be used as in Valentine et al., *JAMA* 258:2881-2885 (1987), the contents of which are incorporated herein by reference. Again, in the absence of a positive reaction to the immunizing dose of liposomes comprising the allergen, for example, within 15-20 minutes of injection, the immunizing dose can be progressively increased, e.g., by ten-fold, with the next immunizing dose.

The frequency of immunization can be determined by monitoring the serum immunoglobulin level of the allergic individual, for example, serum IgG, or IgE, at periodic intervals and inject the next immunizing dose at an appropriate time, e.g., when IgE level begins to rise. The frequency of immunization can also be arbitrarily set at certain times, for example, initially once a week until a threshold immunizing dose is reached, then once every two to four weeks or longer. Within the context of the present invention, a threshold immunizing dose is the dose of liposomes comprising allergens used for injection into an allergic individual that is capable of eliciting a large location reaction, for example, defined in Creticos et al., *JAMA* 258:2874-2880 (1987), the contents of which are incorporated herein by reference.

The allergens to be used in the present invention can be purchased from commercially available sources. The identity of the nearest available source can be obtained from local allergists who routinely administer allergy shots to patients. In the alternative, an up-to-date list of manufacturers licensed to sell allergens in the form of allergeneic extracts can be obtained from the United States Food and Drug Administration, Office of Biologics, located at 8800 Rockville Pike, Bethesda, Md. 20892. Examples of such manufacturers include Allergy Laboratories, Inc. (Oklahoma City, Okla.), Creer Laboratories, Inc. (Lenoir, N.C.) and 3M Diagnostic Systems, Inc. (Mountain View, Calif.).

A liposome in solution within the present invention is generally in the shape of a spherical vesicle having one or several concentric layers of lipid molecule each of which is represented by the formula XY, wherein X is a lipophobic-hydrophilic moiety and Y is a lipophilic-hydrophobic moiety. In solution, the concentric layers are arranged such that the hydrophilic moiety remains in contact with an aqueous phase. For example, when aqueous phases are present both within and without the liposome, the lipid molecules will align themselves in a bilayer, XY-YX formation, known as a lamella.

The liposomes suitable for use in the present invention comprise at least one of a group consisting of phospholipids, glycolipids and cholesterol. Preferably, the phospholipids are diacylglycerols in which at least one acyl group comprises at least twelve carbon atoms, preferably between about fourteen to about twenty-four carbon atoms. It is also preferred that at least one head group of the phospholipids, i.e., the portion of the molecule that contains the phospho-group. is a phosphocholine, a phosphoethanolamine, a phosphoserine or a phosphoinositol.

The liposomes to be used in accordance with the present invention can be neutral or can carry a positive charge or preferably a negative charge. Stearylamine can be used in the lipid mixture to confer a positive charge and dicetyl phosphate can be used to confer a negative charge on the liposomes.

The lipids that can be used herein can be purchased from commercially available sources. For example, dimyristoyl phosphatidylcholine ("DMPC") can be purchased from Sigma Chemical Co.; dicetyl phosphate ("DCP") from K and K Laboratories (Plainview, N.Y.); cholesterol ("Chol") from Calbiochem-Behring (La Jolla, Calif.); dimyristoyl phosphatidylgylcerol ("DMPG") and other lipids can be purchased from Avanti Polar Lipids, Inc. (Birmingham, Ala.)

Some of the commercially available sources of glycolipids that can be used are: galactocerebroside (beef brain) from supelco (Bellfonte, Pa.), Sigma and PL Biochemicals; DL-dihydrogalactocerebroside, N-lignoceroyl from Calbiochem-Behring; lactocerebroside, DL-dihyrolactocerebroside, N-lignoceroyl from Calbiochem; ceramide trihexoside (human erythrocyte) from Supelco; ceramide tetrhexoside (globoside) (human erythrocyte) from Supelco; digalactosyl diglyceride (plant) from Supelco, Sigma and PL Biochemicals; gangliosides (mixed) (beef brain) from Calbiochem-Behring, Supelco, Sigma and PL Biochemicals; gangliosides from Supelco.

Stock solutions of lipids in chloroform or chloroform/methanol can be stored at about −20° C. Preferably, chloroform is used as the only solvent since it is more readily evaporated than methanol. Phospholipids from natural sources, such as egg or soybean phosphatidylcholine, brain phosphatidic acid, brain or plant phosphatidylinositol, heart cardiolipin, and plant or bacterial phosphatidylethanolamine are preferably not used as the primary phosphatide because of the instability and leakiness of the resulting liposomes.

The different lipids that make up the liposomes within the present invention can be in any molar ratio. In one preferred embodiment, the molar ratio of DMPC:DMPG:Chol is about 0.9:0.1:0.75.

Liposomes used herein can be prepared by various known techniques. For example, liposomes can be prepared according to the method of Bangham et al., as described in *J. Mol. Biol.* 13:238-252 (1965); the method of Gregoriadis, as described in "Liposomes" in *DRUG CARRIERS IN BIOLOGY AND MEDICINE*, pp. 287-341 (G. Gregoriadis ed. 1979); the method of Deamer and Uster as described in "Liposome Preparation: Methods and Mechanisms" in *LIPOSOMES* (M. Ostro ed. 1983); the reverse-phase evaporation method, as described in Szoka, Jr. and Papahadjopoulos, in "Procedure for Preparation of Liposomes with Large Internal Aqueous Space and High Capture by Reverse-Phase Evaporation," *Proc. Natl. Acad. Sci.* USA 75:4194-98 (1978), the contents of all of which are incorporated herein by reference. The aforementioned methods differ in their respective abilities to entrap aqueous material and their respective aqueous space-to-lipid ratios.

In a preferred embodiment, liposomes can be made by mixing together the lipids to be used in a desired proportion in a container, e.g., a pear-shaped flask, having a volume ten times greater than the volume of the anticipated suspension of liposomes. Using a rotary evaporator, the solvent is removed at approximately 40° C. under negative pressure. The vacuum obtained from a filter pump aspirator attached to a water faucet may be used. The solvent normally is removed within about 2 to 5 minutes. The composition can be dried further in a desiccator under vacuum. The dried lipids are usually discarded after about 1 week because of its tendency to deteriorate with time.

The dried lipids can be rehydrated at approximately 30 mM phospholipid in sterile, pyrogen-free water by shaking until all the lipid film is off the glass. The aqueous liposomes can be then separated into aliquots, each placed in a vaccine vial, lyophilized and sealed under vacuum. The lyophilized liposomes prepared in the foregoing manner can be rehydrated and reconstituted in a solution of the allergen and diluted to an appropriate concentration with a suitable solvent, e.g., Dulbecco's phosphate buffered saline lacking $CaCl_2$ and $MgCl_2 \cdot 6H_2O$ ("DPBS", GIBCO Laboratories, Grand Island, N.Y.). Optionally, liposomes containing allergens can be separated from liposomes without allergens in a column, e.g., a Sepharose 6B (Pharmacia) column.

In a preferred embodiment, a lipid mixture in chloroform can be dried under vacuum in a pear-shaped flask. After addition of a small quantity of acid-washed 0.5 mm glass beads, the liposomes can be swollen in solutions of the allergen diluted in, e.g., 0.15M NaCl by 2 minutes of vigorous shaking in a vortex mixer Allergen that have not be encapsulated can be removed by centrifugation at about 12,000 to 15,000 × g for about 10 minutes at 20° C. The liposomes can be washed in 0.15M NaCl and centrifuged as above. The washed liposomes can be suspended in 0.15M NaCl at a total phospholipid concentration of 20 mM. The amount of allergen encapsulated can be determined by established chemical techniques. For example, the amount of protein allergen can be determined by the method of Lowry.

The method to be selected for preparing liposomes also depends on the size of liposomes desired. In one embodiment of the present invention, larger liposomes can be used since they can be taken up by macrophages much sooner than smaller liposomes. The more energy that is used to produce the liposomes the smaller the liposomes. For example, sonication of a lipid mixture in producing the liposomes will result in smaller liposomes than vigorous vortexing of the mixture.

Optionally, lipid A can be incorporated into the liposomes before allergen encapsulation. Lipid A is a lipoidal constituent of lipopolysaccharide ("LPS") from Gram-negative bacteria, e.g., *Escherichia coli*, Salmonella and Shigella. As used herein, lipid A comprises "native" lipid A isolated from the Gram-negative bacteria, in a pyrogenic amount, e.g., 20 nmol of lipid A phosphate per micromol of liposomal phospholipid (hereafter "lipid A-20"), in a nonpyrogenic amount, e.g., 0.2 nmol of lipid A per micromol of liposomal phospholipid (hereafter "lipid A-0.2") and a monophosphoryl fraction of lipid A that has reduced pyrogenicity (hereafter "MP lipid A").

Lipid A can be obtained from LPS by established laboratory techniques. In a preferred embodiment, lipid A is prepared in the manner of Alving et al., 2 *LIPOSOME TECHNOLOGY* 157-175, G. Gregoriadis, ed. (CRC Press 1984). Essentially, LPS is prepared by phenol-extraction or by trichloroacetic acid treatment of such bacterial cells. Alternatively, lipid A can be purchased from commercially available sources, e.g., Calbiochem-Behring; List Biological Laboratories, Inc. (Campbell, Calif.) and Ribi Immunochem Research, Inc. (Hamilton, Mont.). LPS is similarly available from commercial sources, e.g., Difco (Detroit, Mich.), List Biological Laboratories, Inc. and Ribi Immunochem Research, Inc.

For extraction of lipid A from LPS, the LPS can be heated in a boiling water bath for about two hours in about 1% acetic acid in an amount of about 10 mg of LPS per ml. The precipitate formed is washed three times with distilled water by centrifugation at 4° C. and then lyophilized. To purify the lipid A so obtained, an aqueous solution of about 0.5% triethylamine ("TEA") is used for solubilization of lipid A in the water phase. This solution is allowed to stand for about 10 to 30 minutes. The phases are separated, with or without centrifugation at about 12,000 × g for about 10 minutes. The resulting purified lipid A is chloroform soluble and may be analyzed for phosphate content by standard techniques. In general, about 1 microgram of chloroform-soluble lipid A from *E. coli*, strain 0111 LPS (from Difco) contains about 0.3 nmol of phosphate, and 1 microgram from Salmonella LPS contains about 0.7 nmol of phosphate.

For incorporation of lipid A into the liposomes in accordance with the present invention, lipid A can be added to the flask together with the other lipids used for making liposomes, i.e., DMPC, Chol and DCP, and all the lipids can be dried together.

To encapsulate allergens in the liposomes, liposomes with or without lipid A that have been previously dried are mixed and rehydrated in the presence of an allergen and a medium suitable for injection, e.g., DPBS. If desired, the rehydrated liposomes comprising the allergens can be sonicated, for example, for 10 sec. to obtain smaller liposomes. The liposomes can be passed through a separation column to separate allergen-containing liposomes from non-allergen-containing liposomes, for example, in a Sepharose 6B (Pharmacia) column. The amount of allergen encapsulated can be determined by standard analytical techniques. The preparation can be diluted to a predetermined concentration and can be administered, as an agent for desensitization against the allergen, either orally or injected intravenously, intradermally, subcutaneously, intramuscularly, or intraperitoneally.

Optionally, the above-described preparation of liposomes comprising an allergen, with or without lipid A can be adsorbed to an aluminum hydroxide absorptive gel (hereafter also referred to as "alum"). The alum can be diluted to an appropriate concentration in DPBS and mixed with the liposomes. Adsorption can proceed either for about 1 hr at room temperature or about 12 hr at 4° C. After adsorption, sufficient supernatant is discarded to yield a concentration of about 0.8 mg to about 1 mg/ml of aluminum. Optionally, aluminum phosphate or gamma aluminum oxide can be used in place of aluminum hydroxide.

Immune response to administration of the desensitizing agent can be monitored by established immunologic techniques, preferably by enzyme-linked immunosorbent assay (hereafter "ELISA"). In a preferred embodiment, wells of polystyrene microtiter plates can be each coated with 0.1 microgram of allergen in about 0.01 M phosphate buffered saline ("PBS") at pH 7.4. Approximately 18 hr later, the contents of the wells can be aspirated, and the wells filled with blocking buffer, i.e., about 1.0% BSA, 0.5% casein, 0.01% thimerosal and 0.005% phenol red in PBS, and held for 1 hr at room temperature. Sera to be tested, for example, human sera, can be diluted in blocking buffer and aliquots of each dilution added to triplicate wells prepared above. After a 2-hr incubation at room temperature, the contents of the wells are aspirated and the wells washed approximately three times with PBS-Tween 20. About 50 microgram of horseradish peroxidase conjugated to, e.g., goat-anti-human immunoglobulin G ("IgG" Bio-Rad Laboratories, Richmond, Calif.) which is diluted to 1:500 With 10% heat-inactivated fetal calf serum in PBS, is then added to each well. After 1 hr, the contents of the wells are aspirated, the wells washed three times with PBS-Tween 20, and 150 microliter of peroxidase substrate in buffer is then added to each well. The absorbance at 414 nm can be determined 1 hr later with an ELISA plate-reader device, e.g., TITERTEK MULTISKAN-R (Flow Laboratories, Inc., McLean, Va.).

The following examples are given by way of illustration to facilitate a better understanding of the invention and are not intended to limit the invention.

EXAMPLE 1

Desensitization of an allergic person to ragweed pollen.

In one embodiment of the present invention, an individual allergic to ragweed pollen can be injected subcutaneously or intramuscularly in an upper arm with an initial immunizing dose of liposomes comprising ragweed pollen extracts in an amount comprising about 0.1 microgram of antigen E, in a volume of 0.05 ml. About 20 minutes after injection, the site of injection can be examined and the result can be recorded.

If the individual reacted positively to the injection, for example, with local redness and swelling exceeding about 10 mm in diameter, the individual can be given the same or lower dose at the next treatment, which can be scheduled for one week later. If a lower dose of liposomes comprising allergens is desired, the initial dose can be reduced by half by dilution in a suitable diluent appropriate for injection.

If the individual fails to react to the initial immunizing dose within about 20 minutes after injection, the next immunizing dose can be increased, e.g., by ten-fold, to be given one week later. This procedure of injection, examination and determination of the next immunizing dose can be repeated, until a threshold dose for the individual is reached. Such a threshold dose is reached when the immunizing dose cannot be further increased because of continual positive reactivity to the immunizing dose.

Upon reaching the threshold dose, the individual can be maintained on that dose or a slightly lower dose and can be injected at less frequent intervals, e.g., monthly, every two months, three months, etc., depending on the individual's ragweed-specific IgE and/or IgG level, which can be monitored using an ELISA format.

EXAMPLE 2

Desensitization of an allergic person to stinging insect venom.

An individual allergic to stinging insect venom, e.g., venoms of honeybee, yellow jacket, yellow hornet, bald-faced hornet, and Polistes wasps can be desensitized with the liposomes of the present invention comprising an amount of the venom as in Example 1, but with the following modifications:

The initial immunizing dose can comprise a dose of 0.1 microgram of each relevant venom. The immunizing dose can be increased through subsequent weekly increments, e.g., from 0.1 microgram to 1.0 microgram to 3.0 microgram administered at 20-minute intervals in the first week, to 10.0, 20.0, 40.0, 70.0, and 100 micrograms, respectively, in subsequent weeks. There can be a stepped progression of the injection interval to four weeks after the individual reaches the 100 microgram dose. A four-week interval can be maintained during the first six to 12 months of treatment. This interval can be lengthened to six or eight weeks if the serum level of venom-specific IgG antibody remain higher than an acceptable minimum concentration (4 to 5 microgram/mL).

What is claimed is:

1. An agent for desensitization of man or animals against an allergen comprising liposomes that comprise an allergen, wherein said allergen is at least one selected from the group consisting of food allergens, drug allergens, venom allergens, plant allergens, animal allergens and extracts thereof, either in an unconjugated form or in the form of a hapten conjugated to a carrier.

2. An agent as claimed in claim 1, wherein said liposomes comprise an adjuvant.

3. An agent as claimed in claim 1, wherein said liposomes are adsorbed onto at least one of the group consisting of aluminum hydroxide, aluminum phosphate, and gamma aluminum oxide.

4. An agent as claimed in claim 1, wherein said allergen is at least one selected from the group consisting of venom allergens, plant allergens, animal allergens and extracts thereof, either in an unconjugated form or in the form of a hapten conjugated to a carrier.

5. An agent as claimed in claim 4, wherein said allergen is at least one plant allergen selected from the group consisting of tree pollen, grass pollen, weed pollen and extracts thereof, either in an unconjugated form or in the form of a hapten conjugated to a carrier.

6. An agent as claimed in claim 1, wherein said agent is administered orally or injected either intramuscularly, intravenously, intraperitoneally, intradermally, and subcutaneously.

7. An agent as claimed in claim 1, wherein carrier molecule is at least one selected from the group consisting of bovine serum albumin, thyroglobulin and tetanus toxoid.

8. An agent as claimed in claim 1, wherein said allergen is at least one selected from the group consisting of honeybee venom, yellow jacket venom, yellow hornet venom, bald-faced hornet venom and wasp venom.

9. A method for desensitization of man or animals by administration of an agent comprising liposomes that comprise an allergen as claimed in claim 1.

10. A method for desensitization of man or animals by administration of an agent comprising liposomes that comprise an allergen.

11. A method as claimed in claim 10, wherein said agent is administered orally or injected either intramuscularly, intravenously, or intraperitoneally.

12. A method as claimed in claim 10, wherein said liposomes comprise lipid A.

13. A method as claimed in claim 10, wherein said liposomes are adsorbed onto aluminum hydroxide.

14. A method as claimed in claim 10, wherein said agent is administered at intervals of at least about 4 weeks.

15. A method as claimed in claim 10, wherein said agent is administered at least at 0 week, 4 weeks, 8 weeks, 52 weeks and semi-annually or once a year thereafter.

16. A method as claimed in claim 10, wherein said allergen is at least one selected from the group consisting of food allergens, drug allergens, venom allergens, plant allergens, and animal allergens.

17. A method as claimed in claim 10, wherein said agent is administered subcutaneously or intramuscularly.

18. A method as claimed in claim 16, wherein said allergen is at least one selected from the group consisting of plant allergens, animal allergens and venom allergens.

19. A method as claimed in claim 18, wherein said allergen is at least one venom allergen selected from the group consisting of honeybee venom, yellow jacket venom, yellow hornet venom, bald-faced hornet vacuum and wasp venom.

* * * * *